United States Patent [19]

Brown et al.

[11] Patent Number: 5,827,850
[45] Date of Patent: Oct. 27, 1998

[54] 1,2,4-BENZOTRIAZINE OXIDES FORMULATIONS

[75] Inventors: Stephen Brown, Morpeth; Edward Baker, Chathill, both of England

[73] Assignee: Sanofi Pharmaceuticals, Inc., New York, N.Y.

[21] Appl. No.: 837,637

[22] Filed: Apr. 21, 1997

Related U.S. Application Data

[63] Continuation-in-part of Ser. No. 533,424, Sep. 25, 1995, abandoned.

[51] Int. Cl.⁶ ...................................................... A61K 31/53
[52] U.S. Cl. ............................................................... 514/243
[58] Field of Search ................................................. 514/243

[56] References Cited

U.S. PATENT DOCUMENTS 3,980,779  9/1976  Ley et al. ................................. 514/243
5,175,287  12/1992  Lee et al. ................................. 544/183

*Primary Examiner*—Jerome D. Goldberg
*Attorney, Agent, or Firm*—Michael D. Alexander; Mary P. Bauman; Paul Dupont

[57] ABSTRACT

Disclosed are: aqueous parenteral formulations for the treatment of cancer tumors comprising 1,2,4-benzotriazine 1,4-dioxides in a citrate buffer; and method of cancer tumor treatment.

14 Claims, No Drawings

1,2,4-BENZOTRIAZINE OXIDES FORMULATIONS

This application is a continuation-in-part of application Ser. No. 08/533,424, filed Sep. 25, 1995, now abandoned.

BACKGROUND OF THE INVENTION

1. Field of the Invention

The present invention relates to the field of treatments for cancer tumors. More particularly, the present invention relates to treatment of cancer tumors with 1,2,4-benzotriazine oxides contained in an aqueous buffered vehicle.

2. Reported Developments 1,2,4-Benzotriazine oxides are known compounds. U.S. Pat. No. 3,980,779 discloses 3-amino-1,2,4-benzotriazine-1,4-di-oxide compositions having the formula

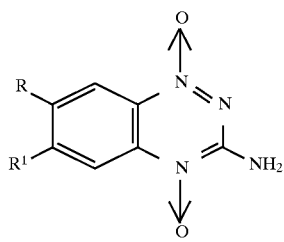

wherein one of R and $R^1$ is hydrogen, halogen, lower alkyl, halo (lower alkyl), lower alkoxy, carbamoyl, sulfonamido, carboxy or carbo (lower alkoxy) and the other of R and $R^1$ is halogeno, lower alkyl, halo (lower alkyl), lower alkoxy, carbamoyl, sulfonamido, carboxy or carbo (lower alkoxy), as antimicrobial composition used to promote livestock growth.

U.S. Pat. No. 5,175,287 issued Dec. 29, 1992 discloses the use of 1,2,4-benzotriazine oxides in conjunction with radiation for treatment of tumors. The 1,2,4-benzotriazine oxides sensitize the tumor cells to radiation and make them more amenable to this treatment modality.

Holden et al (1992) "Enhancement of Alkylating Agent Activity by SR-4233 in the FSaIIC Murine Fibrosarcoma" JNCI 84: 187–193 discloses the use of SR-4233, namely 3-amino-1,2,4-benzotriazine-1,4-dioxide, also known and hereinafter sometimes referred to as tirapazamine, in combination with an antitumor alkylating agent. The four antitumor alkylating agents, cisplatin, cyclophosphamide, carmustine and melphalan, were each tested to examine the ability of tirapazamine to overcome the resistance of hypoxic tumor cells to antitumor alkylating agents. Tirapazamine was tested alone and in combination with varying amounts of each of the antitumor alkylating agents. When SR-4233 was administered just before single-dose treatment with cyclophosphamide, carmustine or melphalan marked dose enhancement leading to synergistic cytotoxic effects on tumor cells was observed.

International Application No. PCT/US89/01037 discloses 1,2,4-benzotriazine oxide as radiosensitizers and selective cytotoxic agents. Other related patents include: U.S. Pat. Nos. 3,868,372 and 4,001,410 which disclose the preparation of 1,2,4-benzotriazine oxides; and U.S. Pat. Nos. 3,991,189 and 3,957,799 which disclose derivatives of 1,2,4-benzotriazine oxides.

Members of 1,2,4-benzotriazine oxides have been found to be effective in the treatment of cancer tumors when used in conjunction with radiation therapy and chemotherapy.

Radiation therapy and chemotherapy, along with surgery, remain the three primary modalities in the treatment of cancer. Radiation therapy and chemotherapy function as alternatives to surgery in the primary control of a variety of neoplasms, where surgery is limited by anatomic consideration. Current knowledge demonstrates that higher cure rates and greater quality of life could be afforded to cancer patients if the effectiveness of radiation therapy and chemotherapy were improved.

One way to improve the effectiveness of radiotherapy or chemotherapy is to take advantage of the hypoxia that exists in tumors—one of the few exploitable difference between normal and tumor tissues. Abnormal development of blood vessels is characteristic of a large number of solid tumors. This abnormal capillary system often results in areas of hypoxia, transient or permanent. In general, hypoxia increases the resistance of a cell, normal or cancerous, to therapy. A method that augments the kill of hypoxic tumor cells (or limits the radiation damage to normal tissues) would improve the therapeutic index of radiation or chemotherapy.

The benzotriazine compounds have been developed to take advantage of this relative hypoxia within the tumor. Tirapazamine, the most promising member of the benzotriazine series to date, is bioreduced under conditions of hypoxia to an active intermediate. This active intermediate can induce DNA damage, which enhances the effects of radiation therapy or chemotherapy and is cytotoxic in its own right. Because adjacent normal tissues are not hypoxic, this bioreduction allows for selective cytotoxic effects on hypoxic tumor cells.

Research has indicated substantial superiority of the benzotriazines over nitroimidazole radiation sensitizers and other bioreductive agents in vitro as shown in Table I.

TABLE I

Hypoxic Cytotoxicity Ratios For Various Bioreductive Drugs In Vitro

| Bioreductive Agent (and type) | Hypoxic Cytotoxicity Ratio[a] | |
|---|---|---|
| | Rodent | Human |
| Tirapazamine (Benzotriazine di-N-oxide) | 75–200 | 15–100 |
| RSU-1069 (Nitroimidazole/Aziridine) | 75–100 | 10–20 |
| Misonidazole (Nitroimidazole) | 10–15 | 15 |
| Porfiromycin (Quinone) | 5–10 | ~10 |
| Nitracrine (Nitroacridine) | 7 | — |
| Mitomycin C (Quinone) | 1–5 | 1–2 |

[a]Hypoxic cytotoxicity ratio = For equivalent levels of cell killing, the ratio of the drug concentration required under aerobic conditions vs. under hypoxic conditions.

Tirapazamine, however, has the drawbacks of insufficient solubility in pharmaceutical vehicles suitable for parenteral administration as well as being unstable in such vehicles. It has been found that the solubility of tirapazamine in water is about 0.81 mg/ml, which would required a large volume of the solution, approximately, 1 liter, to be administered to a patient for providing the proper dose. Attempts to enhance the solubility using surfactants such as Tween 80, and polymers such as Pluronic F68, Povidone and Albumin were unsuccessful with minimal increase in solubility. Solubility enhancement with co-solvents was more successful, however, the proportion of co-solvents necessary to solubilize the expected minimum tolerated dose of tirapazamine would mean infusing significant quantities of co-solvents, for example, up to 120 ml propylene glycol as a 50% v/v propylene glycol/aqueous solution. This large volume of a co-solvent is undesirable in an injectable formulation and risks unwanted clinical affects in a patient.

Tirapazamine also lacks stability on shelf-life: complete degradation occurs after refluxing for less than four hours in 0.1N sodium hydroxide.

The present invention has as its main object to provide an aqueous infusable/injectable formulation which contains sufficient amounts of the anticancer tumor agent and is stable on shelf-life. During our extensive clinical studies of tirapazamine it was realized that without sufficient solubility and stability this very promising drug would not help the countless patients suffering from cancer tumor.

SUMMARY OF THE INVENTION

The present invention provides an aqueous parenteral formulation for the treatment of cancer tumors comprising:

an effective cancer tumor treating amount of a compound of the formula (I)

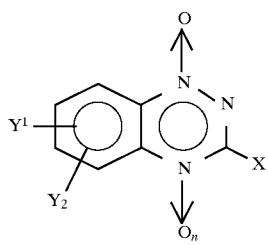

wherein X is H; halogen; alkoxy (C1–C4); hydrocarbyl (C1–C4); OR; $COR^1$; or $NR^2R^3$;

n is 0 or 1; and $Y^1$ and $Y^2$ are independently H; nitro; halogen, alkoxy (C1–C4), hydrocarbyl (C1–C14), optionally interrupted by a single ether linkage; $OR^4$; $COR^5$; $NR^6R^7$; morpholino; pyrrolidino; piperidino; acyloxy (C1–C4); acylamido (C1–C4) and thio analogs thereof; acetylaminoalkyl (C1–C4); carboxy; alkoxycarbonyl (C1–C4); carbamyl; alkylcarbonyl (C1–C4); alkylsulfonyl (C1–C4); alkylphosphonyl (C1–C4); $NR^8R^9O(CO)R^{10}$; $NH(CO)R^{11}$; $O(SO)R^{12}$; $O(POR^{13})R^{14}$; wherein $R-R^7$ can be independently selected from: H, alkyl (C1–C4), acyl (C1–C4), or $R^2$ and $R^3$ or $R^6$ and $R^7$ taken together directly or through a bridge oxygen atom form a morpholino, pyrrolidino or piperidino ring, and where $R^6$ and $R^7$ also can represent hydrocarbyl (C1–C4) unsubstituted or substituted with substituents such as described below, morpholino, pyrrolidino or piperidino, and $R^8$–$R^{14}$ independently represent hydrocarbyl (C1–C4).

X, $Y^1$ and $Y^2$ can be unsubstituted or substituted with substituents such as OH, halogen (Cl, Br, I, F), $NH_2$, alkyl (C1–C4), alkoxy (C1–C4), alkylsecondary amino, dialkyltertiary amino, or a pharmacologically acceptable salt of said compound in a parenterally acceptable buffer having a concentration of from about 0.001M to about 0.1M.

More particularly, the parenteral formulation for the treatment of cancer tumors of the present invention comprises:

of from about 0.500 to about 0.810 g of a compound of the formula (I);

of from about 0.100 to about 9.000 g of sodium chloride;

of from about 0.1 to about 10.00 g of citric acid;

of from about 0.02 to about 3.00 g of sodium hydroxide; and qs to pH 3.0–5.0 in water to 1000 ml.

The preferred anticancer tumor compound of the present invention is tirapazamine, 1,2,4-benzotriazine-3-amine 1,4-dioxide, having the structural formula

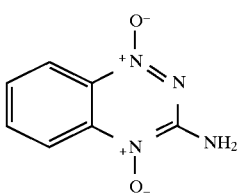

with molecular weight of 178.16 and melting point on decomposition of 220° C.

In the most preferred intravenous formulation each milliliter of solution contains from about 0.7 to about 0.81 mg/ml tirapazamine in an isotonic citrate buffer having a pH of from about 3.7 to about 4.3.

The present invention is also directed to a method of cancer tumor treatment of a patient in need of such treatment comprising administering an effective cancer tumor treating amount of a formulation to said patient.

DETAILED DESCRIPTION OF THE INVENTION

The Antitumor Agents

The present invention provides a composition and a method for treating mammalian cancer tumors, including human cancer tumors, particularly solid tumors. In this aspect of the invention, an effective amount of a compound having Formula I, as defined herein, contained in a citrate buffer solution, is administered to a mammal having a cancer tumor and in need of such treatment from about one half hour to about twenty-four hours before an effective amount of a chemotherapy agent to which the tumor is susceptible is administered to the mammal. Formula I and testing of a compound is described in U.S. application Ser. No. 125,609 filed on Sep. 22, 1993, the disclosure of which in its entirety is incorporated herein by reference.

In the preparation of the formulation of the present invention, extensive studies were conducted to provide sufficient solubility of the cancer tumor compound and render the formulation stable on shelf-life as will become clear from the description that follows.

The present invention will be described in particular reference to tirapazamine formulations, however, it is to be understood that the other denoted compounds of the formula (I) are intended to be covered by the claims of the invention.

For example, another preferred anticancer tumor compound of the present invention is 3-(2-methoxyethyl)-1,2,4-benzotriazine 1,4-dioxide having the structural formula

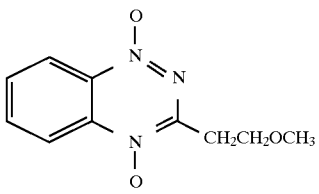

with molecular weight of 221.22.

Solubility Properties of Tirapazamine

The solubility of tirapazamine in water and various vehicles is shown in Table II.

TABLE II

Solubility of Tirapazamine in Aqueous Media

| Solvent | Temp °C. | mg/ml |
|---|---|---|
| Water for Injections | 20 | 1.43 |
| Water for Injections | 15 | 0.85 |
| Normal Saline | 15 | 0.85 |
| Citrate buffer 0.05 M pH 4 (isotonic) | 15 | 0.81 |
| Lactate buffer 0.1 M pH 4 (isotonic) | 15 | 0.90 |
| Tween 80 0.2% w/v | 15 | 0.9 |
| Tween 80 20% w/v | 15 | 1.02 |
| Pluronic F68 20% w/v | 15 | 1.08 |
| Povidone (Kollidon 12PF) 10% w/v) | 15 | 0.95 |
| Albumin 4.5% w/v | 20 | 1.33 |
| Albumin 20% w/v | 20 | 1.71 |
| Glycerol 50% v/v in water | 15 | 2.93 |
| Glycerol | 15 | 4.59 |
| Propylene glycol 50% v/v in water | 15 | 2.58 |
| Propylene glycol | 15 | 3.27 |
| PEG 400 50% v/v in water | 15 | 1.60 |
| PEG 400 | 15 | 5.12 |
| Dimethylformamide 25% v/v in water | 15 | 1.83 |
| 1% Benzyl alcohol:10% ethanol:89% water, v/v | 15 | 1.23 |
| Ethanol 10% v/v in water | 15 | 0.93 |
| Ethanol 50% v/v in water | 15 | 2.32 |
| Ethanol 65% v/v in water | 15 | 2.84 |
| Ethanol 85% v/v in water | 15 | 1.71 |
| Ethanol | 15 | 0.47 |

The limited solubility of 0.81 mg/ml would require up to a liter of fluid to be infused, therefore in order to minimize the fluid volume, solubility needed to be increased. Attempts to enhance the solubility by using surfactants (Tween 80) and polymers (Pluronic F68, Povidone, Albumin) were unsuccessful with minimal increase in solubility.

Solubility enhancement was achieved with co-solvents, however, the proportion of co-solvent necessary to solubilize the expected maximum tolerated dose of tirapazamine (~700 mg) would mean infusing significant quantities of co-solvent (for example up to 120 ml propylene glycol (PG) as 50% v/v PG/aqueous solution).

The physicochemical properties of tirapazamine demonstrate that the molecule is neither highly polar nor highly lipophilic in character. This is illustrated by (i) the partition coefficient (octanol/water) of 0.15 (logP −0.82) and (ii) the observed decomposition on melting at 200° C. which suggests the crystal structure of tirapazamine is strongly bound by intermolecular forces. The planar nature of the molecule would facilitate an ordered stacking with the crystal with intermolecular attractions (charge transfer interactions) between each plane via the nitrogen and oxygen of the N-oxide functions. A hydrated form of tirapazamine can exist where water molecules are hydrogen bonded to the oxygen components.

To predict the solubility of compounds in water-solvent mixtures, various attempts have been made to classify organic solvents using parameters such as dielectric constant, solubility parameter, surface tension, interfacial tension, hydrogen bond donor and acceptor densities, and octanol-water partition coefficient. Values for selected solvents used in tirapazamine solubility studies are given in Table III. These parameters have been used mathematically to predict the solubility of nonpolar solutes by correlating these parameters with the slope of solubility plots constructed form experimental data. Those parameters that reflect the cohesive properties of solvents, such as solubility parameters and interfacial tension, result in the highest correlation with slope, as does the hydrogen bonding ability of the neat co-solvent expressed as the density of proton donating groups or acceptor groups.

TABLE III

Polarity Indices of Solvents (Rubino, J. T. and Yalkowsky, S. H., Cosolvency and Cosolvent Polarity, Pharmaceutical Research, 4 (1987) 220–230)

| | Water | DMSO | DMF | DMA | GLYC | PG | PEG400 |
|---|---|---|---|---|---|---|---|
| Dielectric constant | 78.5 | 46.7 | 36.7 | 37.8 | 42.5 | 32.0 | 13.6 |
| Solubility parameters | 23.4 | 12.0 | 12.1 | 10.8 | 17.7 | 12.6. | 11.3 |
| Interfacial tension dynes/cm | 45.6 | 0.9 | 6.9 | 4.6 | 32.7 | 12.4 | 11.7 |
| Surface tension dynes/cm | 72.7 | 44.0 | 36.8 | 35.7 | 60.6 | 37.1 | 46.0 |
| logP | −4.0 | −1.4 | −0.85 | −0.66 | −2.0 | −1.0 | — |
| Hydrogen bond donor density | 111.0 | 0.0 | 0.0 | 0.0 | 41.1 | 27.4 | 5.6 |
| Hydrogen bond acceptor density | 11.0 | 28.2 | 38.7 | 32.3 | 82.2 | 54.4 | 50.8 | wherein:
DMSO = dimethylsulphoxide
DMF = dimethylformamide
DMA = dimethylacetamide
GLYC = glycerol
PG = propylene glycol
PEG400 = polyethylene glycol 400

At high volume fractions aprotic solvents, e.g., dimethylsulphoxide (DMSO), dimethylformamide (DMF) and dimethylacetamide (DMA), disrupt the water structure through dipolar and hydrophobic effects. Amphiprotic solvents, e.g., glycerol, PEG 400 and propylene glycol (PG) can both self-associate and hydrogen bond with water, consequently, such solvents are not ideally suited for solutes that cannot participate in hydrogen bonding. The partition coefficient of the solute is an indicator for predicting whether co-solvents will be effective. The following equation has been used to successfully predict solubility in various solvent systems:

$$logC_S = logC_O + f(logR + 0.89 logP + 0.03)$$

where $C_S$ and $C_O$ are the solubilities in solvent mixture and water respectively, f is the co-solvent fraction, R is the relative solvent power (typical values being DMF=4, glycerol=0.5) and P is the partition coefficient. As P tends towards unity (logP→0) then no increase in solubility is possible since, $$logC_S = logC_O$$

Since logP for tirapazamine is −0.8, this equation would predict that co-solvents are unlikely to have a significant effect on aqueous solubility. Experiments conducted with these co-solvents results in the finding that solubility of tirapazamine was not significantly enhanced by these co-solvents.

Stability

Stress studies were conducted using multiple autoclave cycles of 21 minutes at 121° C. These studies demonstrated that tirapazamine was more stable in acidic solutions of normal saline or solutions buffered to pH 4 using 0.05M citrate or 0.1M lactate buffer. Tirapazamine was unstable in the presence of phosphate buffer at pH 5.9 and in citrate buffer at pH 6. A shift in the normal saline formulation pH occurred after eight autoclave cycles from 4.5 to 4.9, therefore formulations required some degree of buffering.

Formulations were also stressed by storing at elevated temperatures of 50° C. and 70° C. after a single autoclave cycle of 21 minutes at 121° C. Tirapazamine was found to be unstable in the presence of lactate buffer after storage at 70° C. This instability was not apparent from multiple autoclave stressing. The most stable formulation was found to be 0.05M citrate pH 4.

Formulation of tirapazamine was therefore progressed using citrate buffer. Solubility of tirapazamine at 15° C. required the concentration to be reduced from 1 to 0.5 mg/ml. Further stressing in citrate buffer at pH 3.5, 4.0 and 4.5 was conducted to determine the likely limits for pH. Based on data from this study the limits were set at pH 4.0±0.3.

Based upon the stability data generated, the most stable formulation of tirapazamine was in citrate buffer at pH 4. The solubility of tirapazamine in citrate buffer was 0.81 mg/ml at 15° C. Therefore to limit the volume of infused liquid a maximum concentration of 0.7 mg/ml was used for further formulation development.

The effect of buffer concentration (0.05 or 0.005M) on stability was evaluated by stressing 2×10 L stability batches of tirapazamine (0.7 mg/ml) in citrate buffer at pH 4.0.

Tirapazamine was stable after 2 months in both 0.005M and 0.05M citrate buffer at 50° C. At 70° C., there was evidence of instability with the 0.05M citrate formulation, therefore the lower citrate concentration (0.005M) was chosen for development as the clinical formulation. The clinical formulation used in chemical studies discussed later was as follows:

| | |
|---|---|
| Tirapazamine | 0.700 g |
| Sodium Chloride | 8.700 g |
| Citric Acid | 0.9605 g |
| Sodium Hydroxide | 0.2500 g |
| qs to pH 4.0 in water to 1000 ml. | |

Tirapazamine is stored in clear glass 20 ml ampoules containing 0.7 mg/ml (14 mg) of tirapazamine in the isotonic citrate buffer. The ampoules are stored at 15° C. to 30° C. in light-proof packaging.

Dosing

An acute tolerance study in mice, single and multiple dose studies in rats and dogs and an in vitro myelosuppression study have been conducted with the formulation of the present invention.

In an acute tolerance study in the mouse, the $LD_{10}$ and $LD_{50}$ for tirapazamine were found to be 98 and 101 mg/kg, respectively.

Single and 2-week and 2-month multiple-dose studies were performed in the rat and the dog. Clinical signs and symptoms observed in both species and each regimen included salivation, decreases in white blood cell measurements (including lymphocyte count in the dog), and decreases in red blood cell measurements.

Pharmacology

The effect of tirapazamine on a variety of aerobic and hypoxic cells has been studied in culture to measure the selectivity of tirapazamine cytotoxicity. Tirapazamine (20 $\mu$M) was a potent and selective killer of hypoxic cells in vitro, with hypoxic cytotoxicity ratios of 150, 119 and 52 for hamster, mouse and human cell lines, respectively (1–2 orders of magnitude greater than radiation sensitizers such as nitroimidazoles, mitomycin C and porfiromycin). This cytotoxicity was also observed over a range of oxygen tensions (1%–20% $O_2$; primarily at 1%–4% $O_2$).

In vivo, tirapazamine was equally effective in mouse tumor models as a single 0.30 mmol/kg (160 mg/m$^2$) dose or as multiple 0.08 mmol/kg (43 mg/m$^2$) doses, when used with fractionated radiation (2.5 Gy×8). Tirapazamine was also effective as a single 0.30 mmol/kg (160 mg/m$^2$) dose with a single large (20 Gy) does of radiation. Tirapazamine appeared to be most effective, resulting in several cures in mouse SCCVII tumors, as multiple 0.08 mmol/kg (43 mg/m$^2$) doses given prior to each radiation fraction (2.5 Gy×8); and tirapazamine appeared least effective, resulting in typically less than 1 log of cell kill, when given without radiation. When used with fractionated radiation, tirapazamine produced an effect equal to the effect predicted if tirapazamine were acting upon a separate cell population (hypoxic cells) than the radiation was acting upon (aerobic cells).

The mechanism of action of tirapazamine has been studied in detail and is closely tied to the metabolism of the drug. The illustration below portrays the proposed mechanism of action for tirapazamine-production of a free radical, during reduction to the mono-N-oxide, which causes single- and double-strand breaks in DNA. Under hypoxic conditions, tirapazamine is metabolized to the 2-electron reduction product WIN 64102 (mono-N-oxide; SR 4317) and then to the 4-electron reduction product WIN 60109 (zero-N-oxide; SR 4330). Several studies examining DNA damage repair following treatment with tirapazamine have shown the DNA repair inhibition to be dose-related and similar to that produced by x-rays.

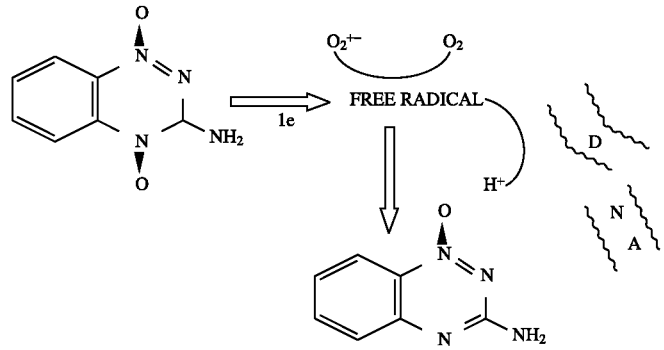

The benzotriazine di-N-oxide tirapazamine was extensively studied both in vitro and in vivo to determine and quantify its effectiveness and to elucidate its mechanism of action.

In Vitro

The effects of tirapazamine on a variety of aerobic and hypoxic cells have been studied in culture to measure the selectivity of tirapazamine cytotoxicity. Chinese hamster ovary cells (CHO-HA-1), mouse cells (C3H 10T½, RIF-1, and SCCVII), and human cell lines (HCT-8, AG 1522, A549 and HT 1080) were used. Tirapazamine (20 $\mu$M) was a potent and selective killer of hypoxic cells in vitro as shown in Table 4.

TABLE 4

In Vitro Cytotoxicity of Tirapazamine to Eight Cell Lines Incubated Under Aerobic or Hypoxic Conditions

| Species | Cell line Name | Sensitivity Index[b] | IC$_{50}$[c] ($\mu$M) | Hypoxic cytotoxicity ratio[a] Cell Line | Species Average |
|---|---|---|---|---|---|
| Hamster | CHO-HA-1 (normal[d]) | 48 | 5 | 100–200 | 150 |
| Mouse | RIF-1 (tumor) | 30 | 3 | 80–100 | |
| | SCCVII (tumor) | 39 | 4 | 160–200 | 119 |
| | C3H 10T1/2 (normal) | 118 | 12 | 75–100 | |
| Human | HCT-8 (tumor) | 94 | 10 | 15–40 | |
| | A549 (tumor) | 280 | 15 | 25–50 | |
| | AG 1522 (normal) | 190 | 13 | 50 | 52 |
| | HT 1080 (tumor) | | 22 | 100 | |

[a]Hypoxic cytotoxicity ratio = Concentration of tirapazamine in air/Concentration of tirapazamine in nitrogen to yield approximately the same survival.
[b]Sensitivity index = Time (in minutes) to reach $10^{-2}$ (1%) surviving fraction at 20 $\mu$M under hypoxic conditions.
[c]IC$_{50}$ = Concentration required to inhibit cell growth by 50% in a 1-hour incubation under hypoxic conditions.
[d]Normal = nontumorigenic.

In Vivo

Tirapazamine Alone

When given alone in vivo in mice, tirapazamine-in single doses-would be expected to produce a relatively small cell kill corresponding to the percentage of tumor cells which are hypoxic. A number of experiments have shown this to be the case, with cell kills typically less than one log (surviving fraction $\geq 1 \cdot 10^{-1}$). For example, the maximum cell kill observed following a single does was in the SCCVII tumor (surviving fraction=$5 \cdot 10^{-1}$), and only a small tumor growth delay of 3 days was produced in the FSaIIC fibrosarcoma.

Multiple doses of tirapazamine given without radiation, might be expected to produce slightly more cell killing than a single does, even at lower doses of tirapazamine. However, the lowest surviving fraction seen in four different mouse tumors was $5 \cdot 10^{-1}$, and down to $5 \cdot 10^{-2}$ in a fifth mouse tumor (RIF-1 tumor).

Tirapazamine with Radiation

In a number of model systems described below, tirapazamine augments the antitumor activity of radiation, assessed by cell killing or tumor growth delay. Tumors tested include FSaIIC, SCCVII, RIF-1, EMT6, and KHT. Tirapazamine augments cell kill when given on a single- or multiple-dose schedule, and when the drug is combined with either single-dose or fractionated radiation.

In one study, the antitumor effect of tirapazamine plus radiation exceeds the additive effect of these two treatments. Augmentation of activity by tirapazamine occurs when the drug is administered form 2.5 to 0.5 hours before radiation or up to 6 hours afterward. In addition to activity against hypoxic cells, tirapazamine radiosensitizes aerobic cells in vitro if the cells are exposed to the drug under hypoxic conditions either before or after radiation.

In one study, treatment with tirapazamine enhanced the antitumor activity of radiation to a greater extent than did the hypoxic cell sensitizer etanidazole.

The oxygen concentration/cytotoxicity curve of tirapazamine appears particularly well suited to combination with radiotherapy. Below approximately 30 torr (mm of Hg) cells become increasingly resistant to damaging effects of radiation. Nitroaromatic and quinone antibiotic radiosensitizers, however, are most effective only at much lower oxygen levels. Thus, they are not toxic to the moderately hypoxic, radioresistant cells present in tumors. By contrast, the cytotoxicity of tirapazamine remains relatively constant over the entire range of oxygen concentrations conferring radio-resistance.

Unlike other radiosensitizers studied to date, the toxicity of tirapazamine decreases at high oxygen concentrations (i.e., those found in normal tissue). In an in vitro system, the toxicity of tirapazamine was at least 50 to >2000 fold higher under hypoxia than under 100% oxygen vapor. Because it is active against a wide range of radio-resistant tumor cells but is not toxic to normal cells with high oxygen concentrations, tirapazamine is selectively cytotoxic to hypoxic tumor cells.

Tirapazamine with Chemotherapy

When tirapazamine (25 to 75 mg/kg IP=83.3 to 250 mg/m$^2$) was administered to mice bearing the FSaIIC fibrosarcoma, some direct tumor cell killing was observed. Addition of tirapazamine (50 mg/kg IP=167 mg/m$^2$) to cyclophosphamide (150 mg/kg IP=500 mg/m$^2$), melphalan (10 mg/kg IP=33 mg/m$^2$), or cisplatin (10 mg/kg IP=33 mg/m$^2$) in this model produced 1.6- to 5.3-fold increases in tumor growth delay.

Effect on Normal Tissue

Female C3H/Km mice were used in two assays to examine the potential that tirapazamine might affect normal tissue sensitivity to ionizing radiation. Both normal skin reaction and leg (thigh) contraction tests were conducted with fractionated radiation. Tirapazamine did not affect the tissues in either assay.

To determine if tirapazamine might affect normal tissue, the right hind limbs of female C3H/Km mice were irradiated with eight fractions (3,4,5 or 6 Gy) over 4 days (once every 12 hours). The mice were injected with either saline or tirapazamine (0.08 mmol/kg=43 mg/m$^2$) 30 minutes before, or immediately after each fraction. Skin reactions over the irradiated thighs were scored three times weekly, from Day 10 to Day 32 after the first irradiation dose. The mice were scored "blinded"—with no knowledge of their treatment group-according to a scale similar to one developed previously [Brown J M, Goffinet D R, Cleaver J E, Kallman R F, "Preferential radiosensitization of mouse sarcoma relative to normal mouse skin by chronic intra-arterial infusion of halogenated pyrimidine analogs", JNCI (1971) 47, 77–89]. No radiosensitization or additive toxicity was produced by the addition of tirapazamine to the radiation treatment as determined by skin reaction.

Having described the invention with reference to its preferred embodiments, it is to be understood that modifications within the scope of the invention will be apparent to those skilled in the art.

What is claimed is:

1. An aqueous parenteral formulation for the treatment of susceptible cancer tumors comprising:

an effective cancer tumor treating amount of a compound of the formula (I)

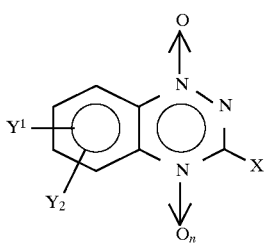

wherein X is H; halogen; alkoxy (C1–C4); hydrocarbyl (C1–C4); OR; COR$^1$; or NR$^2$R$^3$;

n is 0 or 1; and

Y$^1$ and Y$^2$ are independently H; nitro; halogen, alkoxy (C1–C4), hydrocarbyl (C1–C14), optionally interrupted by a single ether linkage; OR$^4$; COR$^5$; NR$^6$R$^7$; morpholino; pyrrolidino; piperidino; acyloxy (C1–C4); acylamido (C1–C4) and thio analogs thereof; acetylaminoalkyl (C1–C4); carboxy; alkoxycarbonyl (C1–C4); carbamyl; alkylcarbonyl (C1–C4); alkylsulfonyl (C1–C4); alkylphosphonyl (C1–C4); NR$^8$R$^9$O(CO)R$^{10}$; NH(CO)R$^{11}$; O(SO)R$^{12}$; O(POR$^{13}$)R$^{14}$;

wherein R–R$^7$ can be independently selected from: H, alkyl (C1–C4), acyl (C1–C4), or R$^2$ and R$^3$ or R$^6$ and R$^7$ taken together directly or through a bridge oxygen atom form a morpholino, pyrrolidino or piperidino ring, and where R$^6$ and R$^7$ also can represent hydrocarbyl (C1–C4) unsubstituted or substituted with substituents selected from those described below, morpholino, pyrrolidino or piperidino, and R$^8$–R$^{14}$ independently represent hydrocarbyl (C1–C4); and X, Y$^1$ and Y$^2$ can be unsubstituted or substituted with substituents selected from OH, halogen (Cl, Br, I, F), NH$_2$, alkyl (C1–C4), alkoxy (C1–C4), alkylsecondary amino, dialkyltertiary amino, or a pharmacologically acceptable salt of said compound in a parenterally acceptable buffer having a concentration of from about 0.001M to about 0.1M and a pH of about 3–5.

2. A method for the treatment of a susceptible cancer tumor in a patient in need of such treatment comprising administering an effective cancer tumor treating amount of a formulation to said patient in need of such treatment, said formulation comprising:

an effective cancer tumor treating amount of a compound of the formula (I)

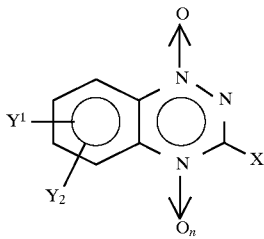

wherein X is H; halogen; alkoxy (C1–C4); hydrocarbyl (C1–C4); OR; COR$^1$; or NR$^2$R$^3$;

n is 0 or 1; and

Y$^1$ and Y$^2$ are independently H; nitro; halogen, alkoxy (C1–C4), hydrocarbyl (C1–C14), optionally interrupted by a single ether linkage; OR$^4$; COR$^5$; NR$^6$R$^7$; morpholino; pyrrolidino; piperidino; acyloxy (C1–C4); acylamido (C1–C4) and thio analogs thereof; acetylaminoalkyl (C1–C4); carboxy; alkoxycarbonyl (C1–C4); carbamyl; alkylcarbonyl (C1–C4); alkylsulfonyl (C1–C4); alkylphosphonyl (C1–C4); NR$^8$R$^9$O(CO)R$^{10}$; NH(CO)R$^{11}$; O(SO)R$^{12}$; O(POR$^{13}$)R$^{14}$;

wherein R–R$^7$ can be independently selected from: H, alkyl (C1–C4), acyl (C1–C4), or R$^2$ and R$^3$ or R$^6$ and R$^7$ taken together directly or through a bridge oxygen atom form a morpholino, pyrrolidino or piperidino ring, and where R$^6$ and R$^7$ also can represent hydrocarbyl (C1–C4) unsubstituted or substituted with substituents selected from those described below, morpholino, pyrrolidino or piperidino, and R$^8$–R$^{14}$ independently represent hydrocarbyl (C1–C4); and X, Y$^1$ and Y$^2$ can be unsubstituted or substituted with substituents selected from OH, halogen (Cl, Br, I, F), NH$_2$, alkyl (C1–C4), alkoxy (C1–C4), alkylsecondary amino, dialkyltertiary amino, or a pharmacologically acceptable salt of said compound in a citrate buffer having a concentration of from about 0.005M to about 0.05M and a pH of about 3–5.

3. An aqueous parenteral formulation for the treatment of susceptible cancer tumors comprising:

of from about 0.500 to about 0.810 g of a compound of the formula (I)

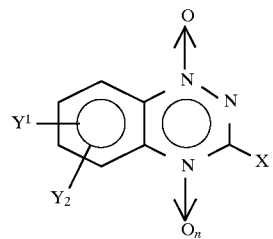

wherein X is H; halogen; alkoxy (C1–C4); hydrocarbyl (C1–C4); OR; COR$^1$; or NR$^2$R$^3$;

n is 0 or 1; and

Y$^1$ and Y$^2$ are independently H; nitro; halogen, alkoxy (C1–C4), hydrocarbyl (C1–C14), optionally interrupted by a single ether linkage; OR$^4$; COR$^5$; NR$^6$R$^7$; morpholino; pyrrolidino; piperidino; acyloxy (C1–C4); acylamido (C1–C4) and thio analogs thereof; acetylaminoalkyl (C1–C4); carboxy; alkoxycarbonyl (C1–C4); carbamyl; alkylcarbonyl (C1–C4); alkylsulfonyl (C1–C4); alkylphosphonyl (C1–C4); NR$^8$R$^9$O(CO)R$^{10}$; NH(CO)R$^{11}$; O(SO)R$^{12}$; O(POR$^{13}$)R$^{14}$;

wherein R–R$^7$ can be independently selected from: H, alkyl (C1–C4), acyl (C1–C4), or R$^2$ and R$^3$ or R$^6$ and R$^7$ taken together directly or through a bridge oxygen atom form a morpholino, pyrrolidino or piperidino ring, and where R$^6$ and R$^7$ also can represent hydrocarbyl (C1–C4) unsubstituted or substituted with substituents selected from those described below, morpholino, pyrrolidino or piperidino, and R$^8$–R$^{14}$ independently represent hydrocarbyl (C1–C4); and X, Y$^1$ and Y$^2$ can be unsubstituted or substituted with substituents selected from OH, halogen (Cl, Br, I, F), NH$_2$, alkyl (C1–C4), alkoxy (C1–C4), alkylsecondary amino, dialkyltertiary amino, or a pharmacologically acceptable salt of said compound in a citrate buffer having a concentration of from about 0.005M to about 0.05M;

of from about 0.100 to about 9.000 g of sodium chloride;

of from about 0.9000 to about 10.00 g of citric acid of from about 0.200 to about 3.000 g of sodium hydroxide; and qs to pH 3.0–5.0 in water to 1000 ml.

4. A method for the treatment of a susceptible cancer tumor in a patient in need of such treatment comprising administering an effective cancer tumor treating amount of the formulation of claim 3.

5. An aqueous parenteral formulation for the treatment of susceptible cancer tumors comprising:

an effective cancer tumor treating amount of 1,2,4-benzotriazine-3-amine 1,4-dioxide in a citrate buffer having a concentration of from about 0.005M to about 0.05M and a pH of about 3–5.

6. The aqueous parenteral formulation of claim 5 wherein said citrate buffer has a pH of from about 3.7 to 4.3.

7. A method for the treatment of a susceptible cancer tumor in a patient in need of such treatment comprising administering an effective cancer tumor treating amount of the formulation of claim 5.

8. An aqueous parenteral formulation for the treatment of susceptible cancer tumors comprising: an effective cancer tumor treating amount of 3-(2-methoxyethyl)-1,2,4-benzotriazine 1,4-dioxide in a citrate buffer having a concentration of from about 0.005M to about 0.05M and a pH of about 3–5.

9. The aqueous parenteral formulation of claim 8 wherein said citrate buffer has a pH of from about 3.7 to 4.3.

10. A method for the treatment of a susceptible cancer tumor in a patient in need of such treatment comprising administering an effective cancer tumor treating amount of the formulation of claim 8.

11. An aqueous parenteral formulation for the treatment of susceptible cancer tumors comprising:

of from about 0.500 to about 0.810 g of 1,2,4-benzotriazine-3-amine 1,4-dioxide;

of from about 5.000 to about 9.000 g of sodium chloride;

of from about 0.9000 to about 10.00 g of citric acid of from about 0.200 to about 3.000 g of sodium hydroxide; and qs to pH 3.7–4.3 in water to 1000 ml.

12. A method for the treatment of a susceptible cancer tumor in a patient in need of such treatment comprising administering an effective cancer tumor treating amount of the formulation of claim 11.

13. An aqueous parenteral formulation for the treatment of susceptible cancer tumors comprising:

0.700 g of 1,2,4-benzotriazine-3-amine 1,4-dioxide;

8.700 g of sodium chloride;

0.9605 g of citric acid;

0.2500 g of sodium hydroxide; and qs to pH 4 in water to 1000 ml.

14. A method for the treatment of a susceptible cancer tumor in a patient in need of such treatment comprising administering an effective cancer tumor treating amount of the formulation of claim 13.

* * * * *